United States Patent [19]

Kimpara et al.

[11] Patent Number: 5,019,155
[45] Date of Patent: May 28, 1991

[54] HERBICIDAL GRANULAR COMPOSITIONS

[75] Inventors: Masaomi Kimpara, Hamamatsu; Kaiji Kawai, Toyohashi; Hiroshi Kikuchi; Masai Sato, both of Iwaki, all of Japan

[73] Assignee: American Cyanamid Company, Stamford, Conn.

[21] Appl. No.: 380,846

[22] Filed: Jul. 14, 1989

[30] Foreign Application Priority Data

Jul. 15, 1988 [JP] Japan .................................. 63-175305

[51] Int. Cl.$^5$ ............................................. A01N 33/04
[52] U.S. Cl. .................................... 71/121; 71/DIG. 1
[58] Field of Search ........................... 71/DIG. 1, 121

[56] References Cited

U.S. PATENT DOCUMENTS

| | | |
|---|---|---|
| 3,274,052 | 9/1966 | Yaffe et al. ...................... 71/DIG. 1 |
| 3,980,463 | 9/1976 | Muramato et al. ............. 71/DIG. 1 |
| 4,082,537 | 4/1978 | Dudkowski ..................... 71/DIG. 1 |
| 4,101,582 | 7/1978 | Lutz et al. ............................. 71/121 |

*Primary Examiner*—Glennon H. Hollrah
*Assistant Examiner*—John D. Pak
*Attorney, Agent, or Firm*—John W. Hogan, Jr.

[57] ABSTRACT

The present invention provides fine granular compositions of pendimethalin which are non-dusting and non-staining.

7 Claims, No Drawings

HERBICIDAL GRANULAR COMPOSITIONS

BACKGROUND OF THE INVENTION

The present invention relates to novel herbicidal compositions of N-(1-ethylpropyl)-3,4-dimethyl-2,6-dinitroaniline, (pendimethalin). Customarily dinitroaniline herbicides such as pendimethalin are formulated as emulsifiable concentrates, flowables, wettable powders or the like which are diluted in a spray tank. Although these formulations offer the advantage that they can be applied evenly on the ground as a spray, they require handling, measuring and mixing of a spray solution prior to application.

While the application of a granular formulation to the soil does not require the additional handling before application, granules are difficult to apply uniformly on the ground.

One way to maximize the uniformity of a granular application is to use finer granules, which can be applied on the ground more uniformly. However, the carrier's particles become finer or fragile. Increased dustiness, in the case of the dinitroaniline herbicides which are highly colored, can result in staining.

It is an object of this invention to provide fine granular compositions of pendimethalin which may be applied uniformly to the soil which are non-dusting and non-staining.

SUMMARY OF THE INVENTION

The present invention provides herbicidal fine granular compositions comprising N-(1-ethylpropyl)-3,4-dimethyl-2,6-dinitroaniline (pendimethalin); an organic solvent; and spherical clay granular carriers having an average diameter in the range of about $60\mu$ to $750\mu$. The fine herbicidal granular non-dusting and non-staining compositions of this invention provide improved distribution of pendimethalin when applied to the soil compared to larger conventional granular compositions.

Uniquely it has been found that admixing a solution of pendimethalin dissolved in a high boiling organic solvent, preferably having a boiling point in a range of about 150° C. to 350° C., with a ball type spherical granular carrier having an average particle size in a range of about $60\mu$ to $750\mu$ results in a non-dusting and non-staining fine granular composition which may be applied uniformly.

Preferred compositions of the present invention comprise on a weight basis
about 0.5% to 5.0% pendimethalin;
1.0% to 10.0% solvent having a boiling point of about 150° C. to 350° C.;
and a sufficient amount of a spherical carrier having an average particle size in a range of $63\mu$ to $710\mu$, to total 100%.

Pendimethalin is a dinitroaniline herbicide which is known to exist in two polymorphic crystalline forms. U.S. Pat. Nos. 4,082,537 and 4,150,969, both incorporated herein by reference, describe compositions which are molecular solutions of pendimethalin and 1.0% to 2.0% of $C_6$–$C_8$ sulfosuccinates and ethoxylated $\beta$-diamines respectively, and their use in wettable powder compositions to avoid formation of less desirable larger orange crystalline forms. These stabilized forms of pendimethalin are preferred for use in the compositions of the present invention.

Solvents suitable for use in the compositions of the invention should have boiling points high enough to minimize evaporation and deposition of pendimethalin on the surface of the granule, with those solvents having boiling points in a range of about 150° C. to 350° C. being preferred. Polyalkyl aromatics such as dimethylnaphthaline, esters of fatty acids such as methyl oleate, and phenyl alkyl substituted aliphatic hydrocarbons such as phenyldimethylphenyl ethane, as well as mixtures and blends of high boiling aromatic compounds which are commercially available from the petroleum industry under a variety of names; and mixtures of these solvents are preferred for use in the compositions of this invention.

Spherical granules for use in the compositions of the invention are prepared by granulating a carrier, a binder, and water using a high speed drum, high speed agitating granulator, pan type granulator, Nauta Mixer, V-type cone mixer or the like, drying the resulting granules in a temperature range of about 40° C. to 180° C. and removing under-sized particles and/or dust and oversized particles, for example by passing through a series of screens or by air classification methods, and collecting the resulting spherical granules having the desired average particles average size of $62\mu$ to $710\mu$.

Carriers suitable for use in the preparation of the fine spherical granules employed in the compositions of this invention include clays such as:

Polygorskite group: attapulgite, sepiolite, polygorskite;
Kaoline group anauxite, dickite, kaolinate, nacrite;
Montmorillonite group: beidellite, bentonite (montmorillonite), nontronite, saponite;
Illite group: mica, vermiculate;
as well as zeorite, volcanic ash, diatomite, calcium carbonate and the like;

with the use of carriers having an average particle size of less than 100 mesh being preferred, with kaolinate, zeolite, and bentonite being most preferred carriers. Binders preferred for use in the compositions of the present invention include: polyvinyl alcohol (PVA), carboxymethyl cellulose (CMC), phenol resin, and hydroxypropyl cellulose (HPC).

The hardness, sorptivity, particle size and apparent density of the spherical granule can be adjusted by varying the kind of clay, the kind and quantity of binders, quantity of water, and the rotation speed and time of the granulation process.

The non-dusting, non-staining herbicidal fine granular compositions of the invention may then be prepared by admixing a solution of stabilized or unstabilized pendimethalin in the high boiling solvent(s) above. Additional agents such as non-ionic, anionic, and cationic surfactants and/or wetting agents and mixtures thereof which are commonly employed in agricultural formulations may be incorporated into the herbicidal fine granules at this stage prior to drying the resulting compositions.

The invention is further illustrated by the following non-limiting examples.

EXAMPLE 1-6

Preparation of Compositions of the Invention i. Preparation of fine spherical granules Fifty kilogram batches of various fine spherical granules are prepared by granulating the ingredients listed in Table I below, and collecting those granules in the 20 mesh to 80 mesh range.

ii. Preparation of herbicidal fine granules

Pendimethalin, 2.67 g (75.4% purity), stabilized with 0.04 g of sodium dioctylsulfosuccinate, is dissolved in 3.5 g of organic solvents listed in Table II below.

The solution is sprayed on 100 g of carrier granules, selected from Table I below, which is tumbling in a bench scale cement type blender. The products are dried at 60° C. for three hours in an oven.

Utilizing the above procedure and the spherical granule carriers and organic solvents listed in Table I and II, yields the herbicidal fine granular compositions listed in Table III below.

TABLE I

| Granules | Clay | Weight % | Binder | Weight % | Water wt % | Granulator type |
|---|---|---|---|---|---|---|
| A | kaolinate | 88.0 | polyvinyl alcohol | 1.3 | 10.7 | high speed drum |
| B | kaolinate | 86.9 | carboxymethyl cellulose | 0.8 | 12.3 | high speed drum |
| C | zeolite | 86.4 | phenyl resin | 1.3 | 12.3 | high speed drum |
| D | zeolite | 86.8 | hydroxypropyl cellulose | 0.9 | 12.3 | pan |
| E | bentonite | 87.4 | polyvinyl alcohol | 0.4 | 13.2 | pan |

TABLE II

| Solvent | Organic solvents Description |
|---|---|
| OS-1 | Phenyldimethylphenyl ethane |
| OS-2 | Dimethylnaphthaline |
| OS-3 | Methyl oleate |
| OS-4 | Acetone |
| OS-5 | Xylene |

TABLE III

Herbicidal fine granular compositions

| Example | Organic solvents | Carrier |
|---|---|---|
| 1 | OS-1 | A |
| 2 | OS-1 | B |
| 3 | OS-1 | C |
| 4 | OS-2 | A |
| 5 | OS-2 | D |
| 6 | OS-3 | E |

EXAMPLE 7-11

Comparative Examples

Utilizing the procedure described in Examples 1-6 above, unstabilized pendimethalin (2.67 g, 75.4%) in various solvents (3.5 g), listed in Table IV below is admixed with each 100 g of both fine spherical granule and non-spherical granule carriers listed in Table IV below to give the comparative compositions listed in Table IV below.

TABLE IV

Comparative compositions

| Comparative Example | Carrier | Solvent |
|---|---|---|
| 7 | Kaolinated mined, crushed, screened | OS-1 |
| 8 | A - spherical (from Table I) | OS-4 |
| 9 | B - spherical (from Table I) | OS-5 |
| 10 | Pumice mined, crushed, screened | OS-2 |
| 11 | Silica sand mined, crushed, screened | OS-5 |

EXAMPLE 12

Dust and Stain Tests

100 Grams of each sample described in Tables III and IV above, is packed in a polyethylene bottle container and kept at 5° C., room temperature and 45° C. The degree of "dust" and "stain" is determined for freshly prepared and aged samples based on the following methods:

(1) Cloth stain test

A 2 g sample is placed in a petri dish and covered with a white cloth and capped. The dish is turned over and shaken 30 times vigorously. A yellow stain on the white cloth is observed. The cloth is shaken out and observed again.

(2) Field test—stain

Wearing a clean white robe, one kilogram of each sample is placed in a "Cyclone" hand applicator (Kyoritsu). The cyclone is hung and sprayed. After finishing, the amount of stain on the applicator's hands and the white robe is observed and rated on the scale indicated below.

| | |
|---|---|
| − | No stain |
| ± | Acceptable level of stain |
| + | Not acceptable stain |
| ++ | Severe stain |
| +++ | Very severe stain |

The results of these experiments, summarized in Table V, demonstrate improved dusting and staining characteristics of the compositions of the invention over extended periods of time.

TABLE V

| | Cloth stain test | | | | Field test Before aging |
|---|---|---|---|---|---|
| Example No | Before aging | After aging at 5° C. for 3 months | After aging at r.t. for 3 months | After aging at 45° C. for 3 months | |
| 1 | − | − | − | − | − |
| 2 | − | − | − | − | − |
| 3 | ± | ± | ± | ± | − |
| 4 | − | ± | − | ± | − |
| 5 | − | ± | − | ± | − |
| 6 | − | ± | − | ± | − |
| 7 | +++ | +++ | +++ | +++ | +++ |
| 8 | − | + | ++ | +++ | − |
| 9 | − | + | ++ | +++ | − |
| 10 | − | + | ++ | ++ | ++ |
| 11 | − | ++ | +++ | +++ | ++ |

EXAMPLE 13

Biological Efficacy

Volcanic ash soil is placed in a plastic pot, 176 cm² (16×11×7 cm). About 100 seeds of *Digitaria adsen-*

*dense* and *Alopecurus aequalis* are sown at three centimeter depth. One day after seeding, the granular samples are delivered by hand uniformly. Three replications are made for each treatment. Twenty days after treatment the tests are rated using the following rating system below.

| Index | Efficacy |
| --- | --- |
| 0 | No effect |
| 1 | Trace effect |
| 2 | Slight effect |
| 3 | Moderate effect |
| 4 | Injury |
| 5 | Definite injury |
| 6 | Herbicidal effect |
| 7 | Good herbicide effect |
| 8 | Approaching complete kill |
| 9 | Complete kill |

The results of these experiments, summarized in Table VI demonstrate biological efficacy of the compositions of the invention.

TABLE VI

| | Rates | Biological efficacy | |
| --- | --- | --- | --- |
| No | g ai/ha | *Digitaria adscendense* | *Alopecurus aequalis* |
| 1 | 670 | 8.5 | 7.7 |
| | 450 | 8.3 | 7.2 |
| | 300 | 7.7 | 5.4 |
| 2 | 670 | 8.5 | 7.7 |
| | 450 | 8.3 | 6.8 |
| | 300 | 8.1 | 5.4 |
| 3 | 670 | 8.5 | 7.7 |
| | 450 | 8.4 | 7.2 |
| | 300 | 8.1 | 5.4 |
| 4 | 670 | 8.5 | 7.5 |
| | 450 | 8.3 | 7.2 |
| | 300 | 7.7 | 4.5 |
| 5 | 670 | 8.5 | 7.7 |
| | 450 | 8.3 | 7.2 |
| | 300 | 8.1 | 5.4 |
| 6 | 670 | 8.5 | 7.5 |
| | 450 | 8.3 | 6.8 |
| | 300 | 7.9 | 5.4 |

What is claimed is:

1. Herbicidal fine granular compositions comprising on a weight to weight basis about 0.5% to 5.0% of N-(1-ethylpropyl)-3,4-dimethyl-2,6-dinitroaniline(pendimethalin); about 1.0% to 10.0% of an organic solvent having a boiling point greater than 150° C.; about 85% to 98.5% of a spherical granular carrier having an average diameter in a range of about 60μ to 750μ; and about 0% to 2% of a stabilizing agent.

2. The composition according to claim 1 wherein the organic solvent has a boiling point in the range of about 150° C. to 350° C. and the spherical carrier has an average particle size of about 63μ to 710μ.

3. A composition according to claim 2, wherein pendimethalin is stabilized with 1% to 2% of a sodium dialkyl $C_6$-$C_8$ sulfosuccinate.

4. A composition according to claim 2, wherein said organic solvent is phenyldimethylphenyl ethane, dimethylnaphthaline or methyl oleate or a mixture thereof.

5. A composition according to claim 2, wherein the spherical carrier is prepared by granulating a powdered carrier having an average particle size of less than 100 mesh.

6. A composition according to claim 2, wherein the spherical carrier is granulated using a binder of polyvinylalcohol, carboxymethyl cellulose, phenol resin, hydroxy propyl cellulose or the mixture thereof.

7. A composition according to claim 2, wherein the spherical carrier is granulated using a high speed drum or pan type granulator.

* * * * *